United States Patent [19]

Chang et al.

[11] Patent Number: 5,142,042

[45] Date of Patent: Aug. 25, 1992

[54] PROCESS FOR PREPARING WELL CRYSTALLIZED ALKALI METAL SALTS OF 3, 7-SUBSTITUTED 7-AMINOCEPHALOSPORANIC ACID DERIVATIVES

[75] Inventors: S. K. Chang, Taipei, Taiwan; Q. C. Yang, Mason, Ohio

[73] Assignee: Purzer Pharmaceutical Co., Ltd., Taipei, Taiwan

[21] Appl. No.: 617,804

[22] Filed: Nov. 20, 1990

Related U.S. Application Data

[63] Continuation-in-part of Ser. No. 299,466, Jan. 23, 1989, abandoned.

[51] Int. Cl.$^5$ .............................................. C07D 501/12
[52] U.S. Cl. ...................................... 540/230; 540/215; 540/228
[58] Field of Search ............................. 540/230, 215

[56] References Cited

U.S. PATENT DOCUMENTS 3,822,256  7/1974  Granatek et al. ................... 540/230
4,912,211  3/1990  Bonfanti .............................. 540/222

*Primary Examiner*—Nicholas S. Rizzo
*Attorney, Agent, or Firm*—Morton J. Rosenberg; David I. Klein

[57] ABSTRACT

A process for preparing a well crystallized alkali metal salt of 3, 7-substituted 7-aminocephalosporanic acid derivatives having the general formula:

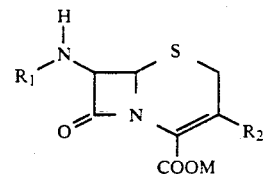

wherein:
$R_1 =$

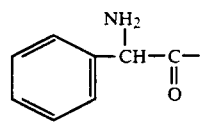

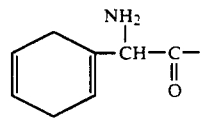

or

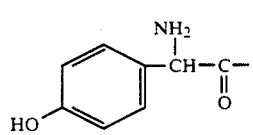

$R^2 =$ CH3 or Cl
$M =$ Na or K from the acid-form derivatives. The process includes preparing a 30% suspension by weight of the acid-form derivative in concentrate alcohol containing 3 to 7% of water by weight, and add an alcoholic solution of alkali base to the suspension under room temperature. The alcohol used to dissolve the base also contains 3 to 7% of water. After a reaction time of 5 to 20 minutes, cool the mixture and let the salt crystallize, and separate the latter from the liquid phase.

5 Claims, No Drawings

PROCESS FOR PREPARING WELL CRYSTALLIZED ALKALI METAL SALTS OF 3, 7-SUBSTITUTED 7-AMINOCEPHALOSPORANIC ACID DERIVATIVES

REFERENCES TO RELATED APPLICATIONS

This Patent Application is a continuation-in-part patent application of U.S. patent application Ser. No. 07/299,466 filed Jan. 23, 1989, now abandoned.

BACKGROUND OF THE INVENTION

The present invention related to a process for preparing a well prepared alkali metal salts of 3, 7 -substituted 7 -aminocephalosporanic acid derivatives.

The derivatives of 3, 7 - substituted 7 - aminocephalosporanic acid are widely used as antibiotics to treat bacterial infections and other diseases caused by, for example staphylococci, streptococci, E. coli and various of Gram negative bacteria as well as parts of the Gram positive bacteria. Among the numerous derivatives, the most commonly used species are:

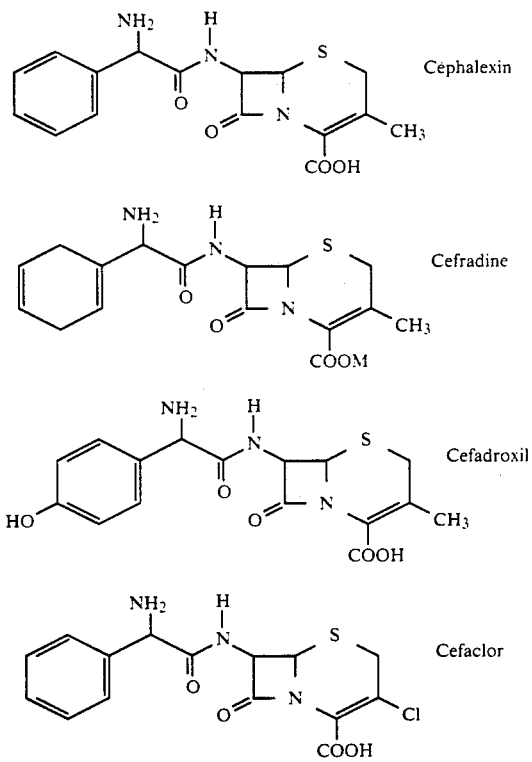

These antibiotics prove effective to many kinds of microbial infection. Unfortunately, due to their low solubility in water, these antibiotics are applied by oral administration only, and cannot be directly injected in their original (acid) form.

Injection has the fastest onset and is the only way to convey a drug to all the portions of the body. By oral administration, a gastro-intestinal absorption is required before the drug enters the blood circulation. The GI absorption also causes several restrictions of oral administration. For example, many drugs are prescribed to administer before or after the meal (and in some cases, accessory ingredients must be used) to protect their negative effects to the GI tract. Also, in oral administration, some special diets are forbidden.

Accordingly, a substitute which has the same pharmaceutical effect as the above antibiotics and which can be applied to patients by injection as well as oral administration is highly desirable.

It is, therefore, the object of the present invention to provide water-soluble antibiotics to meet these requirements.

According to the present invention, the water-solubility is achieved by using the derivatives in form of water-soluble salts, preferably alkali metal salts instead of in acid form.

Furthermore, the object of this invention is to provide a simple and unique process to prepare the water-soluble salts using the available derivatives in acid form as a precursor.

This process involves the neutralization of the acid-form derivative (for example, cefradine) (represented by HD) with an alkaline base (represented by MOH):

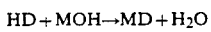

$$HD + MOH \rightarrow MD + H_2O$$

Since the acid-form derivative has a low solubility in solvents, it must at first be made into a suspension, into which a saturated solution of an alkaline base (for example, NaOH) in alcohol is added and mixed to allow the neutralization to take place. Ethyl alcohol is the only ideal medium for the suspension since it is the only organic solvent which has the least toxicity to the human body and does not cause any residual problem. Practically, a 95% alcohol is the idealist medium for the suspension. The alcohol used int eh suspension and the alcohol used to dissolve the base have substantially the same water content. The essential point of this invention is that the water content in the alcohol ranges, operably form 3 to 7%, and preferably form 4 to 6%. Beyond the operable range (greater than 7% or less than 3%) crystallization will be poor or even impossible.

Theoretically, the moral ratio of the derivative HD and the base MOH is 1:1, but preferably, the moral quantity of MOH slightly exceeds that of HD.

The neutralization takes place under ambient temperature (20 to 30 Centigrade, and preferably 20 to 25 Centigrade) the practical concentration of the alcoholic suspension is 30% by weight. The reaction time is about 5 to 20 minutes. Then sow crystals of MD (for example, the sodium slat of cefradine) into the mixture and cool the temperature gradually to −40 to 12 Centigrade to allow the salt crystals to grow until the desired crystalline size is reached the salt-from derivative has a greater stability then its acid-form precursor, and therefore a longer shelf life.

EXAMPLE

Prepare a 30% suspension of cefradine by adding one mole of cefradine in powder from to a 95% alcohol under room temperature. An saturated alcoholic solution containing an excess amount of NaOH (slightly more than 1 mole) is added to the suspension and well mixed. After a few minutes, add seed crystals of the sodium salt of cefradine to the mixture and cool it down to 4 Centigrade when the crystals grow to the desired size, separate them from the liquid phase by filtration.

We claim:

1. A process for preparing a well crystallized salt of 3, 7 - substituted 7 - aminocephalosporanic acid derivative having the following formula:

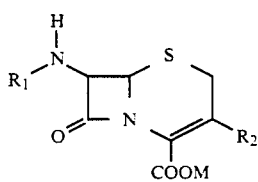

wherein
R1 is an aminocarboxyl group selected from one of the group comprising:

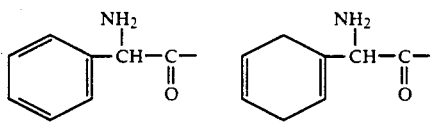

and

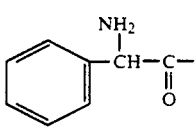

R2 is a substituent selected from the group comprising CH3 and Cl, and
M is an alkali metal,
by neutralizing an alkali base MOH with a derivative in acid form having the following formula:

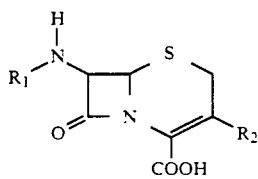

wherein
R1 is an aminocarboxyl group selected from the group comprising:

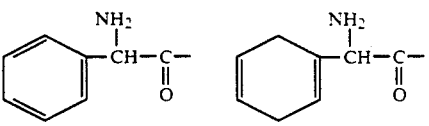

and

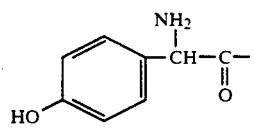

M is an alkali metal;
said process comprising:
preparing a suspension of said acid-form derivative in alcohol by mixing an acid-form derivative in powder form with an ethyl alcohol containing 4 to 6% of water under 20 to 30 Centigrade degree, and add said alkaline base in form of saturated solution water containing alcohol medium to said suspension, with the molar quantity of said base slightly exceeding that of said acid-form derivative, and allowing the resulting salt-form derivative to crystallize, characterized by that said medium contains 93 to 97% of alcohol and 3 to 7% of water.

2. The process according to claim 1, wherein said neutralization takes place under 20 to 25 Centigrade.

3. The process according to claim 1, wherein the concentration of said suspension is 30% by weight.

4. The process according to claim 1, wherein the temperature is cooled to a temperature −40 to 12 Centigrade for crystallization.

5. The process according to claim 1, wherein the reaction time for said neutralization is 5–20 minutes.

* * * * *